United States Patent
Price

[19]

[11] Patent Number: 5,995,861
[45] Date of Patent: Nov. 30, 1999

[54] PRECORDIAL OVERLAY FOR POSITIONING ELECTROCARDIOGRAPH ELECTRODES

[76] Inventor: Michael A. Price, 9988 Voyager Way, Cincinnati, Ohio 45252

[21] Appl. No.: 08/911,818

[22] Filed: Aug. 15, 1997

Related U.S. Application Data

[60] Provisional application No. 60/024,060, Aug. 16, 1996, abandoned.

[51] Int. Cl.⁶ .................................................. A61B 5/0408
[52] U.S. Cl. .......................... 600/372; 600/391; 600/382; 600/392; 600/393; 600/394
[58] Field of Search ..................................... 600/372, 382, 600/384, 386, 388, 389, 390, 391, 393, 394, 509; 607/152, 149, 153

[56] References Cited

U.S. PATENT DOCUMENTS

| | | |
|---|---|---|
| 4,121,575 | 10/1978 | Mills et al. . |
| 4,498,480 | 2/1985 | Mortensen . |
| 4,583,549 | 4/1986 | Manoli .................... 600/396 |
| 4,593,698 | 6/1986 | Athans . |
| 4,854,323 | 8/1989 | Rubin . |
| 5,224,479 | 7/1993 | Sekine . |
| 5,327,888 | 7/1994 | Imran ....................... 600/396 |
| 5,341,806 | 8/1994 | Gadsby et al. . |
| 5,370,116 | 12/1994 | Rollman et al. .......... 600/396 |
| 5,406,945 | 4/1995 | Riazzi et al. ............. 600/394 |
| 5,445,149 | 8/1995 | Rotolo et al. . |
| 5,465,727 | 11/1995 | Reinhold, Jr. . |
| 5,507,290 | 4/1996 | Kelly et al. . |

FOREIGN PATENT DOCUMENTS

| | | |
|---|---|---|
| 0396048 | 11/1990 | European Pat. Off. . |
| 0562208A1 | 9/1993 | European Pat. Off. . |
| 4210684A1 | 10/1993 | Germany . |
| 93162596 U | 2/1994 | Germany . |
| WO97/04703 | 2/1997 | WIPO . |

*Primary Examiner*—John P. Leubecker
*Assistant Examiner*—David M. Ruddy
*Attorney, Agent, or Firm*—Charles R. Wilson

[57] ABSTRACT

A precordial overlay is configured for precise electrode placement on a patient as part of an electrocardiographic test. It is especially useful by emergency medical personnel who are often called upon to obtain an ECG. The precordial overlay has an elongated band having a first generally rectangular-shaped section, a second generally rectangular-shaped and an intermediate section connecting the first and second sections. Electrodes are slidably mounted in the three sections to allow for limited but quick movement from an approximate chest area location to a precise chest area location for a reliable electrocardiographic test.

39 Claims, 3 Drawing Sheets

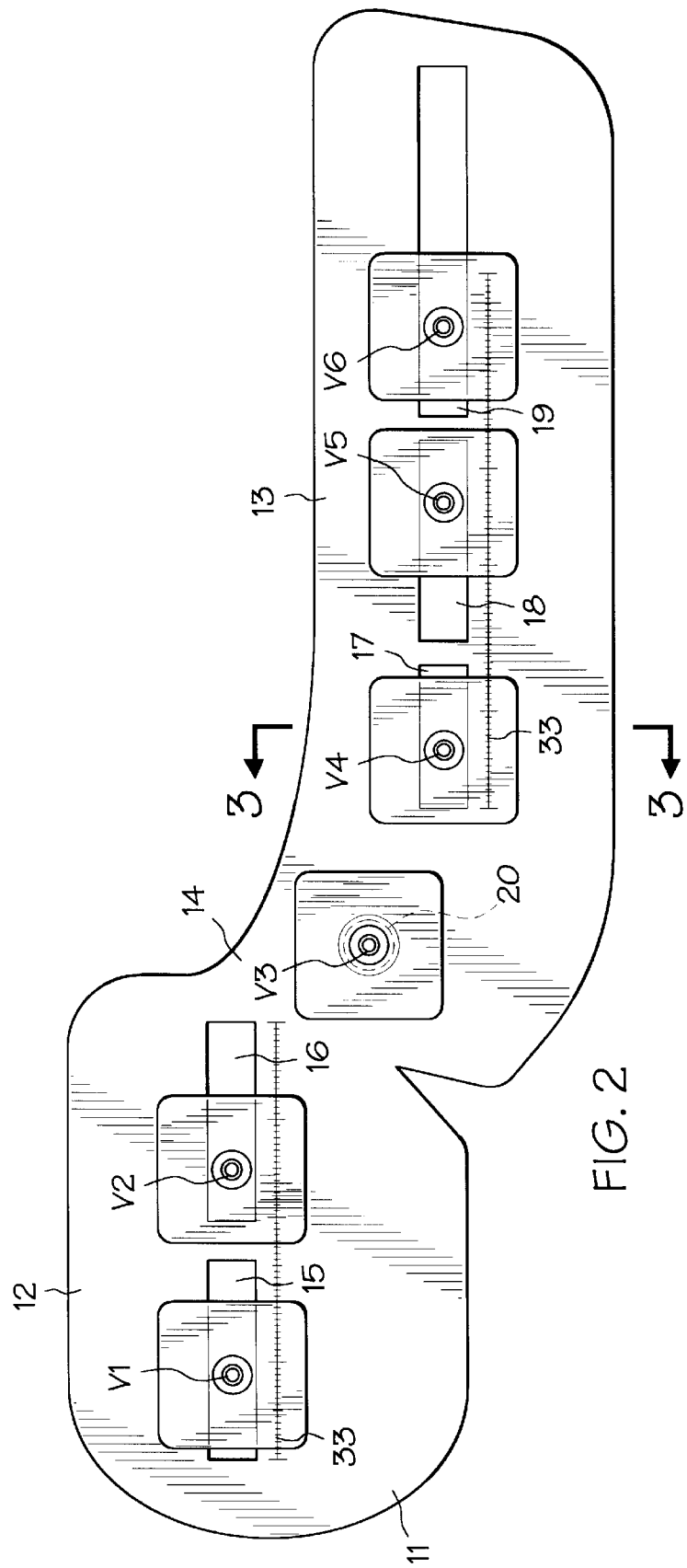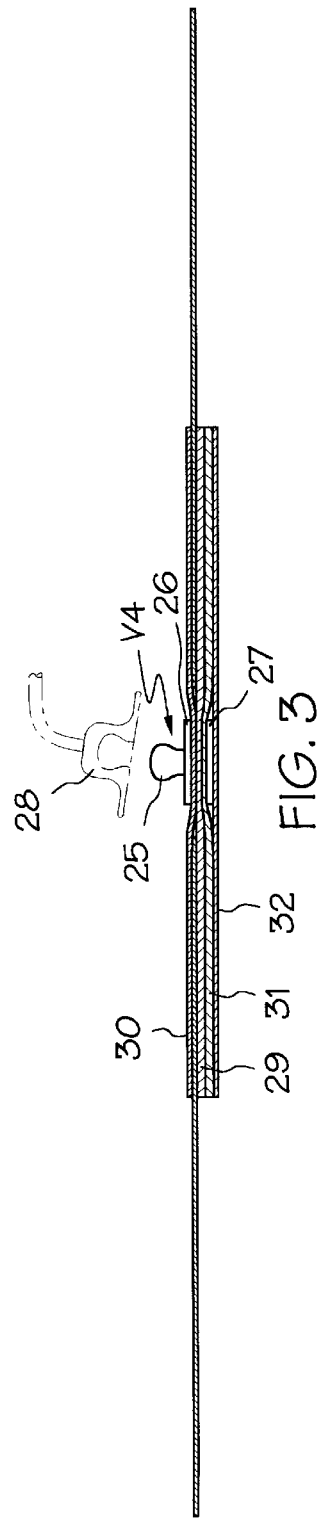

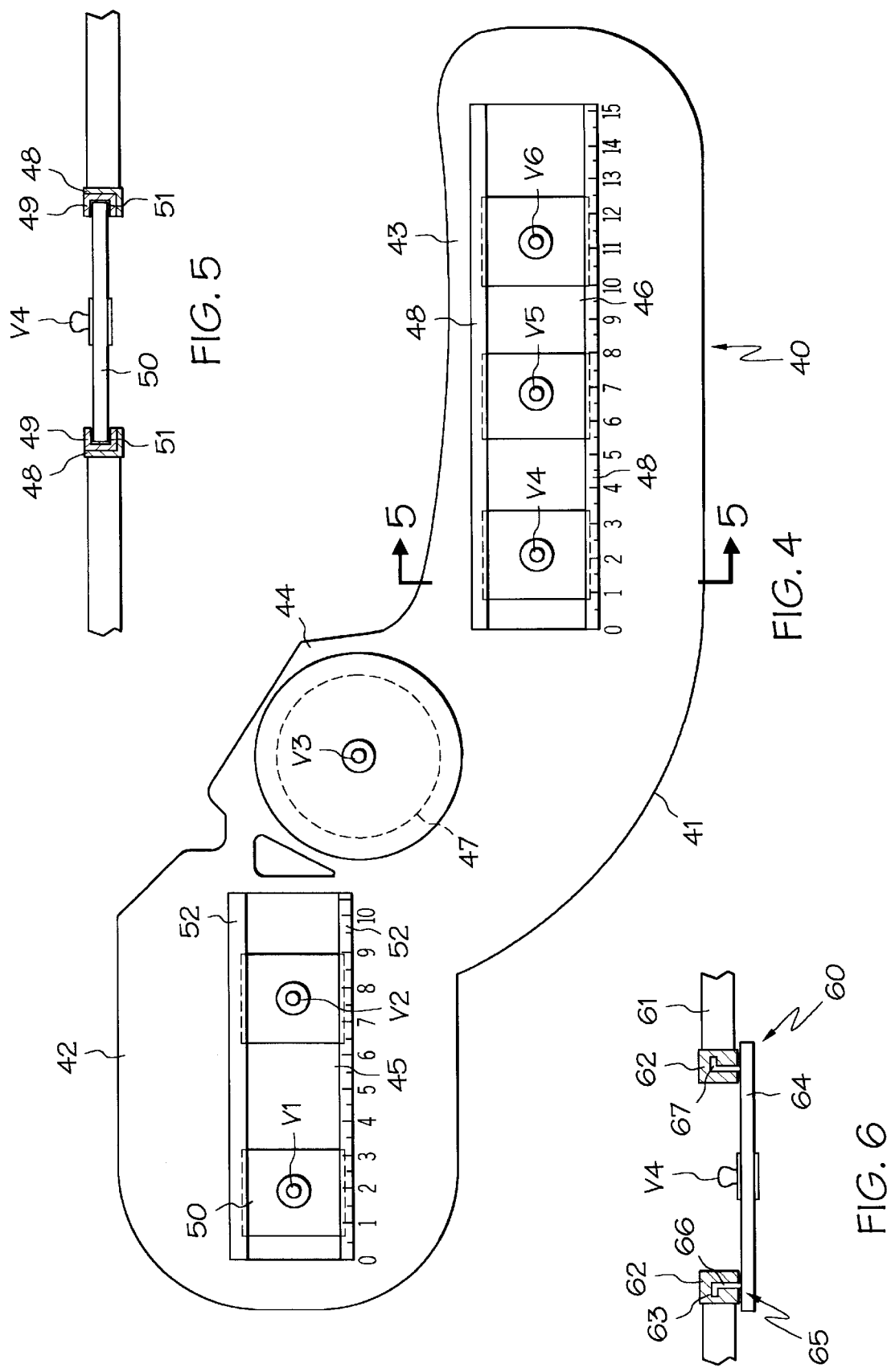

PRECORDIAL OVERLAY FOR POSITIONING ELECTROCARDIOGRAPH ELECTRODES

This application claims the benefit of U.S. Provisional Application No. 60/024,060, filed Aug. 16, 1996 now abandoned.

FIELD OF THE INVENTION

This invention relates to a precordial overlay used with an electrocardiograph to perform an electrocardiographic analysis on a patient. More particularly, the invention relates to a precordial overlay used to quickly and properly position on the patient electrodes which lead to the electrocardiograph.

BACKGROUND OF THE INVENTION

An electrocardiograph is a diagnostic instrument widely used in the medical field. Electric pulses generated by an individual's heart are transformed by the electrocardiograph to a recording on paper or a monitor screen to obtain an electrocardiogram, commonly referred to as an ECG. Trained medical personnel are able to interpret the ECG and detect any abnormality in the individual's heart.

Obtaining an ECG from a patient is a standard procedure used in most routine physical examinations. Emergency medical personnel, e.g. paramedics also are often called upon to obtain an ECG from an individual who has experienced chest pains. It is necessary for the medical personnel to quickly perform the test and follow standard emergency procedures depending on the test results. In some instances, the results in the form of the ECG are transmitted by cellular telemetry to a trained physician. The physician uses the test results to instruct the medical personnel on emergency procedures to be undertaken immediately or possibly to alert hospital personnel to prepare for an incoming patient. Prehospital thrombolytic screening by emergency medical personnel is well recognized in the medical field as an invaluable aid to saving lives.

It is imperative that electrodes which are placed on the patient as a part of obtaining an ECG be properly positioned. Mispositioned electrodes can alter ECG tracings and lead to possible errors in a diagnosis. Current procedures in most locales require that twelve electrodes be properly positioned at various locations on the patient. Positioning of the twelve electrodes by the technician in the physician's office is time consuming, but with patience can be correctly done. The emergency medical personnel who are working under more stressful conditions, however, have a much more difficult time in quickly and precisely positioning the individual electrodes.

There have been attempts by others to develop an article which acts as a aid in quickly and precisely positioning electrodes on a patient as part of an electrocardiographic test. U.S. Pat. Nos. 4,854,323 and 5,341,806 disclose electrode strips which are flexed to follow the patient's chest contour and seemingly to position each electrode in the proper anatomical location. U.S. Pat. Nos. 5,224,479 and 5,445,149 disclose harness-type devices which strap onto the patient's chest. Associated electrodes are said to be properly positioned. U.S. Pat. Nos. 4,121,575, 4,498,480 and 4,593,698 disclose articles which are intended to properly position six electrodes on the patient's chest. Means are provided to fine adjust the precise locations of the six electrodes. It is apparent, though, that quick and reliable electrode positionings are not easily accomplished with the known articles, especially by emergency medical personnel who must work under stressful conditions.

In accord with a demonstrated need, there has been developed a precordial overlay for use primarily by emergency medical personnel to aid them in quickly and precisely positioning electrodes on a patient as part of obtaining an ECG. The overlay is economical to produce, is easy to use and is effective for its intended function.

SUMMARY OF THE INVENTION

A precordial overlay used by medical personnel facilitates the quick and precise positioning of electrodes on a patient. The overlay is an elongated band configured to lie flat on the patient's chest. A set of electrodes is adjustably mounted on the band. The elongated band has a first generally rectangular-shaped section, a second generally rectangular-shaped section, and an intermediate section connecting together the first and second sections. The first section slidably holds two electrodes. The second section slidably holds three electrodes. The intermediate section slidably holds one electrode. All the electrodes are capable of limited adjusting movement in their respective sections of the elongated band prior to use.

The overlay's configuration is conducive to medical personnel placing it on a patient's chest so that its associated electrodes are all in the approximate correct locations for an electrocardiographic test. A series of quick manual manipulations of the electrodes positions each one in the precise location for the test.

BRIEF DESCRIPTION OF THE DRAWINGS

FIG. 2 is a top plan view of the precordial overlay of FIG. 1.

FIG. 3 is a view in section taken along line 3—3 of FIG. 2.

FIG. 4 if a top plan view of a precordial overlay of the invention showing an alternative means for slidably holding electrodes.

FIG. 5 is a view in section taken along line 5—5 of FIG. 4.

FIG. 6 is a view in section of a precordial overlay of the invention showing still another means for slidably holding electrodes.

DETAILED DESCRIPTION OF THE INVENTION

Figure 1:
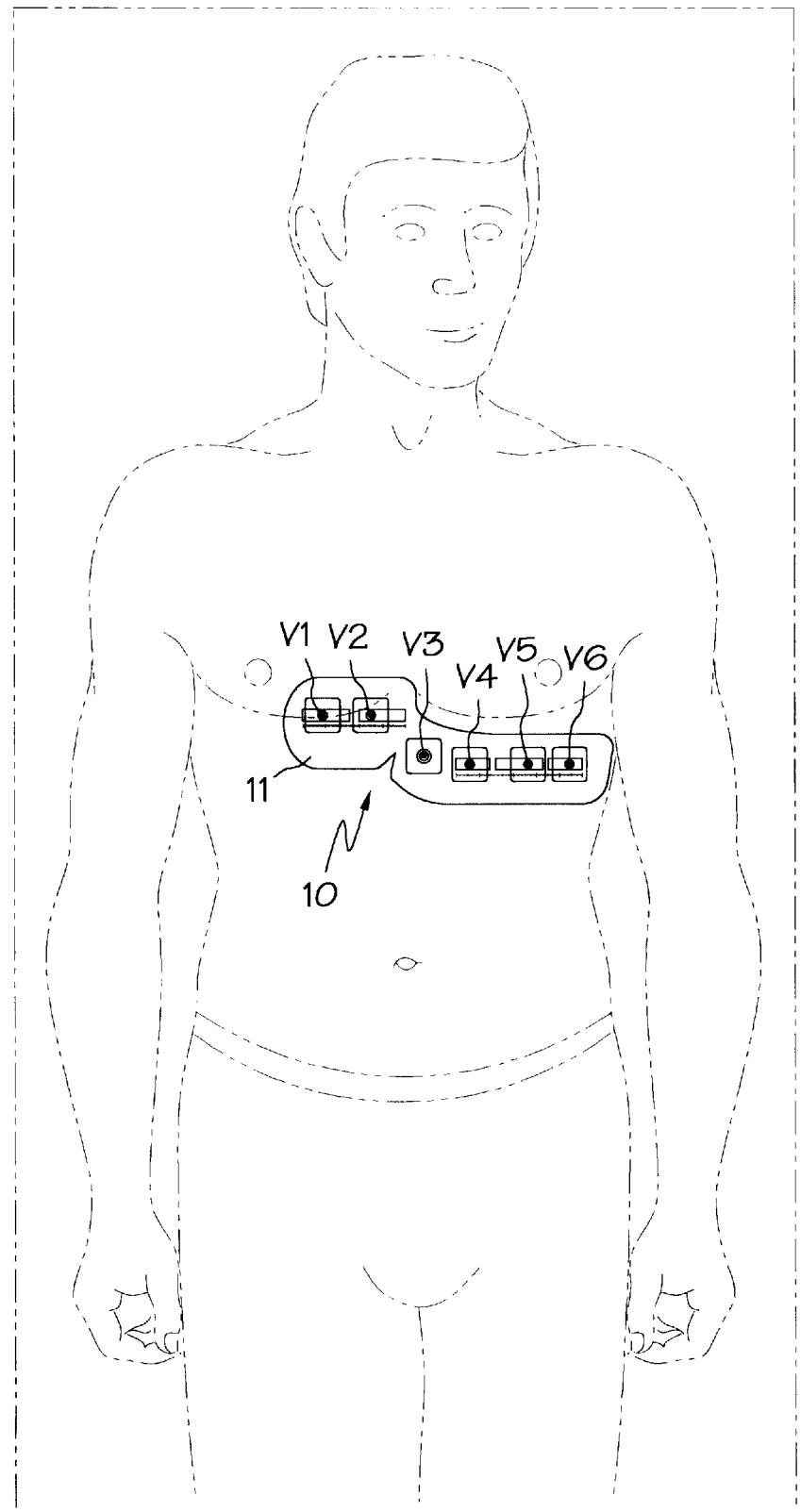
FIG. 1 is an environmental view of a precordial overlay of the invention lying on a prone patient's chest and in position for an electrocardiographic test.

The precordial overlay of the invention is used for quick and proper placement of electrodes on a patient who is having an electrocardiographic test performed. The precordial overlay is primarily used by emergency medical personnel who often must quickly obtain an ECG. It can as well be used by medical personnel in a doctor's office setting as part of a routine physical examination.

The precordial overlay of the invention is depicted in the figures. It comprises an elongated band shaped to overlie a patient's chest and a plurality of electrodes. The electrodes are adjustably mounted on the elongated band. In a highly preferred embodiment of the invention depicted in FIG. 1, five electrodes are slidably positioned in linear cut-outs while one electrode is slidably positioned in a circular cut-out. The precordial overlay's configuration allows emergency medical personnel to place the elongated band onto the patient's chest in the correct gross approximate location and then readily fine adjust the individual electrodes' precise chest location.

Another six electrodes used in conventional twelve lead electrocardiographic tests are not shown in FIG. 1. As well known, they are individually positioned at more remote body locations as currently done and are not a part of the invention.

With reference to FIG. 1, the precordial overlay 10 comprises an elongated band 11 and six electrodes identified by their medical nomenclature as V1–V6. The band 11 is thin and substantially flat. It is also sufficiently flexible to follow the contour of a patient's chest. As best seen in FIG. 2, it has a first generally rectangular-shaped section 12, a second generally rectangular-shaped section 13 and an intermediate section 14. The two generally rectangular-shaped sections are off-set from one another and extend in the same longitudinal direction. The intermediate section 14 connects the first and second generally rectangular-shaped sections 12 and 13. The shape of the band generally coincides with the area of the chest where the electrodes V1–V6 must be positioned to obtain a reliable ECG.

The exact size of the elongated band is dependent on the size of the patient being tested, taking into consideration sex, age and body weight. Generally, because of the electrodes adjustability as described below, two sizes of the precordial overlay are adequate. A larger size is used for adults and a smaller size is used for children under the age of 14. Routine experimentation only is needed to determine the exact dimensions of the elongated band to meet its stated objectives.

The elongated band forming a part of the precordial overlay is made of a non-conductive material. A synthetic polymeric film is preferred because of its low material cost and capability of being given a desired shape by mass production techniques such as die-cutting. The precordial overlay of the invention is disposable primarily because the elongated band is capable of being produced at a reasonable cost. Polyethylene, polypropylene, polyvinylchloride, polyacrylate, polytetrafluoroethylene, nylon and polyester are examples of suitable polymeric films. A polyester film available as Mylar is particularly preferred.

Discreet cut-outs are provided in the body of the elongated band to accommodate the electrodes. Linear cut-outs 15 and 16 in the first generally rectangular-shaped section 12 are configured to receive electrodes V1 and V2 and allow them to laterally slide for precise positioning purposes. The cut-outs 15 and 16 are approximately centered in the first section 12 and run in the same lateral direction. One cut-out can be used in place of the two cut-outs, though is less preferred. Each cut-out 15 and 16 has a length to allow at least about 1.0 inch of electrode lateral movement. Preferably, the cut-outs 15 and 16 are each about 1.5 inches to about 2.5 inches long and about 0.5 inches to about 1.0 inches wide.

Linear cut-outs 17, 18 and 19 in the second generally rectangular-shaped section 13 are configured to receive electrodes V4, V5 and V6 in a manner which allows them to slide within their respective cut-out until properly positioned for the particular patient. Cut-outs 17, 18, and 19 each have a length to allow at least about 1.0 inch of electrode lateral movement. Preferably. cut-out 17 is about 1.5 inches to about 2.0 inches long. Preferably, cut-out 18 is about 1.5 inches to about 2.5 inches long. Preferably, cut-out 19 is about 1.5 inches to about 5.5 inches long. All three cut-outs are about 0.5 inches to about 1.0 inches wide. Each cut-out allows only limited lateral movement of its associated electrode. One cut-out extending the length of cutouts 17–19 can be used instead of the three cut-outs 17–19. However, the three separate cut-outs are preferred to provide added precision in positioning of each of the electrodes V4, V5 and V6.

The cut-out 20 (shown in dotted line form) in the intermediate section 14 is dimensioned to receive an electrode and slidably hold it in position. The cut-out 20 is generally circular in shape with an about 0.5 inches to about 1.5 inches diameter. This relatively small cut-out is sufficient to allow limited movement of the electrode V3 in two directions.

When properly positioned on the patient's chest, the cut-outs 15 and 16 in the first section 12 overlie the patient's fourth rib and the cut-outs 17–19 in the second section 13 overlie the patient's fifth rib. The cut-out 20 in the intermediate section 14 overlies an intercostal area between the fourth and fifth ribs or slightly overlies the fifth rib. It should be apparent that trained medical personnel can very quickly place the precordial overlay on a patient's chest so that the six cut-outs overlie the correct chest area. It is then just a matter of laterally moving electrodes V1, V2, V4, V5 and V6 to a precise location known by the medical personnel. The electrode V3 must be moved laterally and longitudinally, though the precise positioning is readily accomplished.

The electrodes V1–V6 are commercially available. As best seen in FIG. 3, they have a conductive metal post 25, a lower conductive plate 26 and an underlying foam disk 27. The vertically extending post 25 receives a cap head 28 of a lead or wire which is connected to the electrocardiograph. The lower conductive plate 26 can take on different forms. It can, for example, be a flat metal disc as shown. The underlying foam disk 27 is used for comfort reasons in that it is the part of the electrode that contacts the patient's skin during the electrocardiographic test. The disk 27 is saturated with a conducting gel.

Still with reference to FIG. 3, the electrodes illustrated are mounted on a non-conductive pad 29 for ease of handling purposes. A clear plastic sheet layer 30 overlies the pad 29 and surrounds the metal post 25 of the electrode. Its width is greater than that of the cut-out with which it is associated. The plastic sheet 30 is secured to the pad 29 at the conductive plate 26 only, such that its peripheral areas are free or unattached. The plastic sheet's function is to provide a means to slidably hold the pad 29 and its associated electrode V4 in the cut-out 17. The electrode V4 extends up through the cut-out 17. Its associated pad 29 on the underside of the cut-out 17 and the associated plastic sheet 30 on the topside of the cut-out 17 in effect trap the electrode within the cut-out while allowing a sliding movement.

Other electrode styles are known, including clamp electrodes and suction cup electrodes. One additional adhesive style electrode is illustrated and described below with reference to FIGS. 4 and 5. A third adhesive style electrode is illustrated in FIG. 6. Still other styles of electrodes are known and usable in the invention with only minor if any modification to the elongated band to accommodate them.

Further in accord with the invention, an adhesive means is provided to temporarily hold the precordial overlay of the invention to the patient's chest during use. A series of self-stick adhesive strips can be used on the precordial overlay's topside to extend off its peripheral edges and onto the patient's chest. This allows the overlay to be taped to the patient once the overlay is in its proper approximate location. Alternatively, a self-stick adhesive can be provided on the underside of the precordial overlay. The adhesive can cover or appear as strategically placed patches on the underside of the elongated band 11. More preferably and as illustrated, the adhesive is found on the underside of at least some of the individual electrode's non-conductive pads. With reference again to FIG. 3, an adhesive layer 31 extends up to and surrounds the underlying foam disk 27 of the electrode V4. As well known, a removable full piece or two part split backing strip 32 is used to protect the adhesive layer during shipping and storage. When the precordial overlay is ready for placement on the patient, the backing 32 is removed to expose the adhesive layer 31.

Preferably, and with reference to FIGS. 1 and 2, numeric scales 33 are printed onto the elongated band 11 of the precordial overlay. The scales are located just below the cut-outs 15 and 16 in the first generally rectangular-shaped section 12 and below the cut-outs 17–19 in the second generally rectangular-shaped section 13. The numeric scales are used to record precise electrode placements in case a second reading is needed to verify an initial ECG.

In use, the medical emergency personnel initially and temporarily position the elongated band of the precordial overlay 10 on a patient using well known anatomical landmarks, e.g. a sternum notch. The V1 and V2 electrodes are first adjusted for the particular patient. Next, the V4–V6 electrodes are adjusted. The adjustments are made by placing the elongated band onto or at least near the patient's chest. Once the six electrodes are positioned and adjustments made, the backing is removed from the adhesive layer on the underside of each of the pads to expose the adhesive layers. The elongated band is then placed on the patient where it remains until the ECG is obtained. After use, the precordial overlay is discarded.

FIGS. 4 and 5 depict a precordial overlay 40 of the invention having an alternative means of adjustably mounting the electrodes on the elongated band 41. The precordial overlay 40 comprises the elongated band 41 having a first generally rectangular-shaped section 42, a second generally rectangular-shaped section 43 and an intermediate section 44 connecting together the first and second sections. The band 41 has the same shape as the band 11 of the precordial overlay 10. A single cut-out 45 in the first section 42 accommodates the electrodes V1 and V2 and a single cut-out 46 in the second section 43 accommodates the electrodes V4–V6. A circular-shaped cut-out 47 in the intermediate section 44 accommodates the electrode V3.

With particular reference to FIG. 5, a set of plastic slide rails 48 secured to edges of the cut-outs 45 and 46 is provided to slidably receive an electrode pad. Each slide rail 48 has a C-shaped track 49 extending its length. A non-conductive pad 50 with the electrode V4 secured to it is sized so that two parallel edges of the pad fit into the C-shaped tracks 49 and slide therealong. Each pad 50 preferably has an elongated plastic reinforcing strip 51 secured to its two parallel edges to facilitate movement of the pad along the tracks 49 of the rails 48. In a similar manner, a set of slide rails 52 are permanently secured to the cut-out 46 in the second section 43 of the elongated band 41. Electrodes V4, V5 and V6 ride along the rails.

The electrode V3 is slidably mounted in a circular-shaped cut-out 47 found in the intermediate section 44 of the elongated band 41. It operates in the same manner as the electrode V3 in the precordial overlay 10 described above with reference to FIGS. 1–3.

FIG. 6 illustrates still another precordial overlay 60. It comprises an elongated band 61 shaped the same as the elongated band 41 of FIGS. 4 and 5. A track and rail system on the elongated band 61 allows sliding movement of the electrodes V1, V2 and V4–V6. It is used in place of the rail 48 and track 49 depicted in FIGS. 4 and 5. The adjustably mounted electrodes of this embodiment are more stable, though the precordial overlay costs more to produce. Rails 62 are secured to parallel edges of the linear cut-outs. Each rail 62 has an inverted L-shaped track 63 extending along its length. A pad 64 with an electrode V4 in its center is dimensioned to fit under the cut-out in the elongated band 61 of the precordial overlay 60. A set of elongated members 65 is secured to and extend along the top side of the pad near its edges. The members have a substantially vertical ridge 66 which extends up and into the track 63 and a substantially horizontal ledge 67 which extends outwardly from the vertical ridge. The elongated members 65 fits into the inverted L-shaped track 63 of the rails 62 and ride along them to slidably position the pad and its associated electrode.

From the above description, it should be apparent the precordial overlay of the invention serves a very real need, especially in the emergency medical field. Paramedics and other medical personnel can be trained in proper use of the overlay in a relatively short time. Proper placement of electrodes V1–V6 on a patient by a properly trained medical personnel is assured. Furthermore, repeatable ECG test results are a near certainty. The precordial overlay is inexpensive to produce and, resultingly, can be discarded after only one use. This disposable nature of the overlay eliminates any concern for sanitation in that it is not necessary to clean the product after use.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. A precordial overlay for placement on a patient's chest to aid in obtaining quick and accurate positioning of electrodes for an electrocardiographic test, said precordial overlay comprising:

(a) an elongated band having a first generally rectangular-shaped section, a second generally rectangular-shaped section, and an intermediate section connecting together the two generally rectangular-shaped sections so that they are off-set from one another and extend in the same direction, further wherein the first generally rectangular-shaped section has at least one cut-out configured to adjustably receive electrodes, the second generally rectangular-shaped section has at least one cut-out configured to adjustably receive electrodes and the intermediate section has a cut-out to adjustably receive an electrode; and (b) a plurality of electrodes which are slidably mounted in the at least one cut-out of the first generally rectangular-shaped section to slide along a length of the first generally rectangular-shaped section and slidably mounted in the at least one cut-out of the second generally rectangular-shaped section to slide along a length of the second generally rectangular-shaped section and one of which is adjustably mounted in the cut-out of the intermediate section to slide laterally and longitudinally.

2. The precordial overlay of claim 1 wherein six electrodes are slidably mounted in the cut-outs.

3. The precordial overlay of claim 2 wherein the first generally rectangular-shaped section of the elongated band has two cut-outs to each receive one electrode.

4. The precordial overlay of claim 3 wherein the second generally rectangular-shaped section of the elongated band has three cut-outs to each receive one electrode.

5. The precordial overlay of claim 1 wherein each electrode has a substantially vertically extending conductive post for receiving an electrode lead wire and a conductive plate and further each said electrode is mounted on a non-conductive pad, said conductive post having a diameter less than the width of a cut-out in which it is slidably mounted so that the electrode can be grasped and manually moved in said cut-out while the pad slides within or along the underside of said cut-out.

6. The precordial overlay of claim 5 wherein the cut-outs on the first and second generally rectangular sections of the elongated band are linear.

7. The precordial overlay of claim 6 wherein each of the linear cut-outs has a length to allow at least about 1.0 inch of electrode lateral movement.

8. The precordial overlay of claim 1 further comprising an adhesive means for temporarily adhering said precordial overlay to the patient.

9. The precordial overlay of claim 8 wherein each electrode has a metal post to receive an electrode lead wire, a flat metal disc at a lower terminus of the metal post and a foam disk attached to an underside of the flat metal disc and saturated with a conductive gel, further said electrode is mounted on a non-conductive pad and has a plastic sheet covering the pad and surrounding the post to interact with its associated cut-out to retain the electrode in place.

10. The precordial overlay of claim 9 wherein the adhesive means is on the underside of the non-conductive pads.

11. The precordial overlay of claim 10 wherein the adhesive means on the non-conductive pads is an adhesive layer and further has a peel-off backing.

12. The precordial overlay of claim 1 wherein the elongated band is a thin flexible synthetic polymeric film.

13. A precordial overlay for placement on a patient's chest to aid in obtaining quick and accurate positioning of electrodes for an electrocardiographic test, said precordial overlay comprising:

(a) an elongated band having a first generally rectangular-shaped section, a second generally rectangular-shaped section, and an intermediate section connecting together the two generally rectangular-shaped sections so that they are off-set from one another and extend in the same direction, further wherein the first generally rectangular-shaped section has two cut-outs configured to adjustably receive two electrodes, the second generally rectangular-shaped section has three cut-outs configured to adjustably receive three electrodes and the intermediate section has a cut-out to adjustably receive an electrode;

(b) a set of six electrodes, two of which are slidably mounted in the cut-outs of the first generally rectangular-shaped section to slide therein, three of which are slidably mounted in the cut-outs of the second generally rectangular-shaped section to slide therein and one of which is slidably mounted in the cut-out of the intermediate section to slide laterally and longitudinally therein; and (c) an adhesive layer on the underside of the elongated band or electrodes for temporarily adhering the precordial overlay to the patient and further having a peel-off backing on the adhesive layer to protect said backing during shipping and storage of the precordial overlay.

14. The precordial overlay of claim 13 wherein each electrode has a substantially vertically extending conductive post for receiving an electrode lead wire and a flat conductive plate and further each said electrode is mounted on a non-conductive pad, said conductive post having a diameter less than the width of a cut-out in which it is slidably mounted so that the electrode can be grasped and manually moved in said cut-out while the pad slides within or along the underside of said cut-out.

15. The precordial overlay of claim 13 wherein the cut-outs on the first and second generally rectangular sections of the elongated band are linear.

16. The precordial overlay of claim 15 wherein each of the linear cut-outs has a length to allow at least about 1.0 inch of electrode lateral movement.

17. The precordial overlay of claim 13 further comprising an adhesive means for temporarily adhering it to the patient.

18. The precordial overlay of claim 14 wherein the elongated band is a thin flexible synthetic polymeric film.

19. A precordial overlay for placement on a patient's chest to aid in obtaining quick and accurate positioning of electrodes for an electrocardiographic test, said precordial overlay comprising:

(a) an elongated band having a first generally rectangular-shaped section, a second generally rectangular-shaped section, and an intermediate section connecting together the two generally rectangular-shaped sections so that the two generally rectangular-shaped sections are off-set from one another and extend in the same longitudinal direction, further wherein the first generally rectangular-shaped section has at least one linear cut-out extending along a length of said first generally rectangular-shaped section and further said linear cut-out is configured to adjustably receive at least one electrode, the second generally rectangular-shaped section has at least one linear cut-out extending along a length of said second generally rectangular-shaped section and further said linear cut-out is configured to adjustably receive at least one electrode and the intermediate section has a generally circular cut-out to adjustably receive an electrode; and (b) a plurality of electrodes which are adjustably mounted in the at least one cut-out of the first generally rectangular-shaped section to slide therealong and adjustably mounted in the at least one cut-out of the second generally rectangular-shaped section to slide therealong and adjustably mounted in the generally circular cut-out of the intermediate section to slide in two directions therewithin.

20. The precordial overlay of claim 19 wherein the first generally rectangular-shaped section of the elongated band has two cut-outs to each receive one electrode and the second generally rectangular-shaped section of the elongated band has three cut-outs to each receive one electrode.

21. The precordial overlay of claim 19 wherein each electrode has a substantially vertically extending conductive post with an upper terminus for receiving an electrode lead wire and a lower terminus having a conductive plate extending therefrom, further each said electrode is mounted on a non-conductive pad, said conductive post having a diameter less than the width of a cut-out in which it is adjustably mounted so that the electrode can be grasped and manually moved in said cut-out while the pad slides within or along the underside of said cut-out.

22. The precordial overlay of claim 21 wherein each of the linear cut-outs has a length to allow at least about 1.0 inch of electrode movement.

23. The precordial overlay of claim 19 further comprising an adhesive means for temporarily adhering said precordial overlay to the patient.

24. A precordial overlay for placement on a patient's chest to aid in obtaining quick and accurate positioning of electrodes for an electrocardiographic test, said precordial overlay comprising:

(a) an elongated band having a first generally rectangular-shaped section, a second generally rectangular-shaped section, and an intermediate section connecting together the two generally rectangular-shaped sections so that the two generally rectangular-shaped sections are off-set from one another and extend in the same longitudinal direction, further wherein the first generally rectangular-shaped section has two discreet linear cut-outs and each of said two discreet linear cut-outs is configured to adjustably receive an electrode, the second generally rectangular-shaped section has three discreet linear cut-outs and each of said three discreet linear cut-outs is configured to adjustably receive an electrode and the intermediate section has a generally circular cut-out to adjustably receive an electrode; and (b) a set of six electrodes, two of which are individually mounted in the two discreet linear cut-outs of the first generally rectangular-shaped section to slide along said linear cut-outs to correct chest locations, three of which are individually mounted in the three discreet linear cut-outs of the second generally rectangular-shaped section to slide along said linear cut-outs to correct chest locations and one of which is mounted in the generally circular cut-out of the intermediate section to slide in two directions within said generally circular cut-out to a correct chest location.

25. The precordial overlay of claim 24 wherein the elongated band is a thin flexible synthetic polymeric film.

26. The precordial overlay of claim 24 wherein each electrode has a substantially vertically extending conductive post with an upper terminus for receiving an electrode lead wire and with a lower terminus having attached thereto a flat conductive plate, and further each said electrode is mounted on a non-conductive pad, said conductive post having a diameter less than the width of a cut-out in which it is mounted so that the electrode can be grasped and manually moved in said cut-out while the non-conductive pad slides within or along the underside of said cut-out.

27. The precordial overlay of claim 26 wherein each of the electrodes further has a plastic sheet covering the non-conductive pad and surrounding the vertically extending conductive post with free peripheral areas wherein the electrode is mounted in the cut-out such that the non-conductive pad is on an underside of the elongated band and the plastic sheet is on the top side of the elongated band such that the electrode is retained in its operably associated cut-out, yet slides therein.

28. The precordial overlay of claim 24 wherein each of the linear cut-outs in the first and second generally rectangular-shaped sections has a length to allow at least about 1.0 inch of electrode movement therealong.

29. The precordial overlay of claim 28 wherein the cut-outs in the elongated band have operatively associated therewith electrodes V1, V2, V3, V4, V5 and V6 and further wherein (i) a first cut-out in the first generally rectangular section for electrode V1 is about 1.5 inches to about 2.5 inches long and about 0.5 inches to about 1.0 inches wide, (ii) a second cut-out in the first generally rectangular section for electrode V2 is about 1.5 inches to about 2.5 inches long and about 0.5 inches to about 1.0 inches wide, (iii) the cut-out in the intermediate section for electrode V3 has a diameter of from about 0.5 inches to about 1.5 inches, (iv) a first cut-out in the second generally rectangular section for electrode V4 is about 1.5 inches to about 2.0 inches long and about 0.5 inches to about 1.0 inches wide, (v) a second cut-out in the second generally rectangular section for electrode V5 is about 1.5 inches to about 2.5 inches long and about 0.5 inches to about 1.0 inches wide, and (vi) a third cut-out in the second generally rectangular section for electrode V6 is about 1.5 inches to about 5.5 inches long and about 0.5 inches to about 1.0 inches wide.

30. A precordial overlay for placement on a patient's chest, said precordial overlay comprising:

(a) an elongated band having a first generally rectangular-shaped section, a second generally rectangular-shaped section, and an intermediate section connecting together the two generally rectangular-shaped sections so that they are off-set from one another and extend in the same longitudinal direction, further wherein the first generally rectangular-shaped section has at least one linear cut-out extending along a length of said first generally rectangular-shaped section and further each said at least one linear cut-out is configured to adjustably receive at least one electrode, the second generally rectangular-shaped section has at least one linear cut-out extending along a length of said second generally rectangular-shaped section and further each said at least one linear cut-out is configured to adjustably receive at least one electrode and the intermediate section has a cut-out to adjustably receive an electrode; and (b) a plurality of electrodes which are mounted in the at least one cut-out of the first generally rectangular-shaped section to slide therealong and mounted in the at least one cut-out of the second generally rectangular-shaped section to slide therealong and mounted in the cut-out of the intermediate section to slide therewithin, further wherein each electrode has a substantially vertically extending conductive post for receiving an electrode lead wire and a conductive plate and further each said electrode is mounted on a lower non-conductive pad with an upper plastic sheet overlying the lower non-conductive pad and surrounding the vertically extending conductive post with unattached peripheral areas, said conductive post having a diameter less than the width of a cut-out in which it is mounted so that the electrode can be grasped and manually moved in said cut-out while the non-conductive pad slides along the underside of said cut-out and the plastic sheet slides along the topside of said cut-out.

31. The precordial overlay of claim 30 wherein the first generally rectangular-shaped section of the elongated band has two linear cut-outs to each receive one electrode, the second generally rectangular-shaped section of the elongated band has three linear cut-outs to each receive one electrode and the intermediate section has a generally circular shaped cut-out to receive one electrode.

32. The precordial overlay of claim 31 wherein each of the linear cut-outs has a length to allow at least about 1.0 inch of electrode movement therealong.

33. A precordial overlay for placement on a patient's chest, said precordial overlay comprising:

(a) an elongated band of a thin flexible polymeric film having a first generally rectangular-shaped section, a second generally rectangular-shaped section, and an intermediate section connecting together the two generally rectangular-shaped sections so that they are off-set from one another and extend in the same longitudinal direction, further wherein the first generally rectangular-shaped section has two discreet linear cut-outs, each of said two discreet linear cut-outs configured to adjustably receive an electrode, the second generally rectangular-shaped section has three discreet linear cut-outs, each of said three discreet linear cut-outs configured to adjustably receive an electrode and the intermediate section has a cut-out to adjustably receive an electrode; and (b) a set of six electrodes, two of which are individually slidably mounted in the two discreet linear cut-outs of the first generally rectangular-shaped section to slide therealong, three of which are individually slidably mounted in the three discreet linear cut-outs of the second generally rectangular-shaped section to slide therealong and one of which is slidably mounted in the cut-out of the intermediate section to slide in two directions therein, further wherein each electrode has a substantially vertically extending conductive post with an upper terminus for receiving an electrode lead wire and with a lower terminus having attached thereto a flat conductive plate and further each said electrode is mounted on a non-conductive pad with an overlying plastic sheet surrounding the vertically extending conductive post so as to have unattached peripheral areas, said vertically extending conductive post having a diameter less than the width of a cut-out in which it is slidably mounted so that the electrode can be grasped and manually moved in said cut-out while the non-conductive pad slides along the underside of said cut-out and the plastic sheet slides along the topside of said cut-out, said non-conductive pad and plastic sheet retaining the electrode in its cut-out while allowing movement therein for precise chest location purposes.

34. The precordial overlay of claim 33 wherein each of the linear cut-outs has a length to allow at least about 1.0 inch of electrode movement therealong.

35. The precordial overlay of claim 33 wherein the cut-out in the intermediate section of the elongated band is generally circular and has a diameter of from about 0.5 inches to about 1.5 inches.

36. A precordial overlay for placement on a patient's chest, said precordial overlay comprising:

(a) an elongated band of a thin flexible polymeric material to extend across the patient's chest and follow a contour thereof, wherein the elongated band has a first section, an intermediate section and a second section, further wherein the first section has two discreet linear cut-outs, the second section has three discreet linear cut-outs and the intermediate section has a generally circular cut-out, each of said cut-outs configured to adjustably receive an electrode; and (b) a set of six electrodes, two of which are individually slidably mounted in the two discreet linear cut-outs of the first section to slide along said linear cut-outs to correct chest locations, three of which are individually slidably mounted in the three discreet linear cut-outs of the second section to slide along said linear cut-outs to correct chest locations and one of which is slidably mounted in the generally circular cut-out of the intermediate section to slide in two directions within said generally circular cut-out to a correct chest location.

37. The precordial overlay of claim 36 wherein each electrode has a substantially vertically extending conductive post with an upper terminus for receiving an electrode lead wire and with a lower terminus having attached thereto a flat conductive plate, and further each said electrode is mounted on an underlying non-conductive pad with an overlying plastic sheet surrounding the vertically extending conductive post and having unattached peripheral areas, said vertically extending conductive post having a diameter less than the width of a cut-out in which it is slidably mounted so that the electrode can be grasped and manually moved in said cut-out while the pad slides within or along the underside of said cut-out.

38. The precordial overlay of claim 36 wherein each of the linear cut-outs has a length to allow at least about 1.0 inch of electrode movement therealong.

39. The precordial overlay of claim 38 wherein the cut-outs in the elongated band have operatively associated therewith electrodes V1, V2, V3, V4, V5 and V6 and further wherein (i) a first cut-out in the first generally rectangular section for electrode V1 is about 1.5 inches to about 2.5 inches long and about 0.5 inches to about 1.0 inches wide, (ii) a second cut-out in the first generally rectangular section for electrode V2 is about 1.5 inches to about 2.5 inches long and about 0.5 inches to about 1.0 inches wide, (iii) the cut-out in the intermediate section for electrode V3 has a diameter of from about 0.5 inches to about 1.5 inches, (iv) a first cut-out in the second generally rectangular section for electrode V4 is about 1.5 inches to about 2.0 inches long and about 0.5 inches to about 1.0 inches wide, (v) a second cut-out in the second generally rectangular section for electrode V5 is about 1.5 inches to about 2.5 inches long and about 0.5 inches to about 1.0 inches wide, and (vi) a third cut-out in the second generally rectangular section for electrode V6 is about 1.5 inches to about 5.5 inches long and about 0.5 inches to about 1.0 inches wide.

* * * * *